United States Patent [19]

Halpaap et al.

[11] Patent Number: 4,851,531

[45] Date of Patent: Jul. 25, 1989

[54] ISOCYANURATE GROUP-CONTAINING POLYISOCYANATES

[75] Inventors: Reinhard Halpaap, Cologne; Gerhard Klein, Monheim; Roland Richter, Cologne; Hanns P. Müller, Odenthal; Josef Pedain, Cologne; Hans-Joachim Kreuder, Krefeld, all of Fed. Rep. of Germany

[73] Assignee: Bayer Aktiengesellschaft, Leverkusen, Fed. Rep. of Germany

[21] Appl. No.: 74,380

[22] Filed: Jul. 16, 1987

Related U.S. Application Data

[63] Continuation of Ser. No. 831,210, Feb. 20, 1986, abandoned.

[30] Foreign Application Priority Data

Mar. 5, 1985 [DE] Fed. Rep. of Germany ....... 3507719

[51] Int. Cl.$^4$ .......................................... C07D 251/34
[52] U.S. Cl. .................................................. 544/222
[58] Field of Search ................................ 544/193, 222

[56] References Cited

U.S. PATENT DOCUMENTS

| | | | |
|---|---|---|---|
| 3,919,218 | 11/1975 | Schmitt et al. | 260/248 |
| 4,265,798 | 5/1981 | Mishra | 260/32.4 |
| 4,288,586 | 9/1981 | Bock et al. | 528/67 |
| 4,412,073 | 10/1983 | Robin | 544/193 |
| 4,419,513 | 12/1983 | Breidenbach et al. | 544/222 |
| 4,454,317 | 6/1984 | Disteldorf | 544/193 |
| 4,469,867 | 9/1984 | Disteldorf | 544/222 |
| 4,487,928 | 12/1984 | Richter et al. | 544/193 |
| 4,537,961 | 8/1985 | Robin | 544/193 |
| 4,613,685 | 9/1986 | Klein | 560/330 |

FOREIGN PATENT DOCUMENTS

| | | |
|---|---|---|
| 0047452 | 3/1982 | European Pat. Off. . |
| 100129 | 7/1982 | European Pat. Off. . |
| 2616415 | 11/1977 | Fed. Rep. of Germany . |
| 2901479 | 7/1980 | Fed. Rep. of Germany . |
| 3219608 | 9/1983 | Fed. Rep. of Germany . |
| 3402623 | 8/1985 | Fed. Rep. of Germany . |
| 1386399 | 3/1975 | United Kingdom . |
| 1391066 | 4/1975 | United Kingdom . |

*Primary Examiner*—John M. Ford
*Attorney, Agent, or Firm*—Gene Harsh; Joseph C. Gil; Thomas W. Roy

[57] ABSTRACT

The present invention is directed to isocyanato isocyanurates prepared from diisocyanates which contain a sterically unhindered isocyanate group bound to a primary aliphatic carbon atom and a sterically hindered isocyanate group which is bound to a tertiary carbon atom forming part of a cycloaliphatic ring system, said diisocyanate having an NCO content of about 20 to 50% by weight. The present invention is further directed to a process for preparing these isocyanato isocyanurates by catalytic trimerization and the use of the isocyanato isocyanurates in a process for the production of polyisocyanate polyaddition products, preferably two-component polyurethane stoving lacquers.

4 Claims, No Drawings

ISOCYANURATE GROUP-CONTAINING POLYISOCYANATES

This application is a continuation of application Ser. No. 831,210, filed Feb. 20, 1986, abandoned.

BACKGROUND OF THE INVENTION

1. Field of the Invention

The invention relates to new isocyanurate group-containing polyisocyanates based on selected diisocyanates, a process for the production thereof by the trimerization of a proportion of the isocyanate groups of specific aliphatic-cycloaliphatic diisocyanates and the use of the isocyanato isocyanurates as the isocyanate component in polyurethane lacquers.

2. Description of the Prior Art

Isocyanurate group-containing (cyclo-) aliphatic polyisocyanates are of great interest industrially as lacquer polyisocyanates. Whereas low molecular weight aliphatic diisocyanates cannot be used as such in lacquer binders owing to their toxicological properties and their relatively high volatility, isocyanato isocyanurates have a number of advantages. They are oligomers with a low vapor pressure which are substantially free from monomers. They have an isocyanate functionality of ≧3 so that a high degree of cross-linking can be achieved. As aliphatic polyisocyanates, they provide good light-fastness in the coatings obtained from them.

Various processes are known for producing isocyanurate group-containing polyisocyanates. These known processes generally differ in the selection of the trimerization catalysts or in the selection of polyisocyanates to be used during the trimerization reaction (see, for example, GB-P 1,391,066, GB-P 1,386,399, DE-OS 2,325,826, DE-OS 2,616,415, DE-OS 2,806,731, DE-OS 2,901,479, DE-OS 3,100,262, DE-OS 3,219,608, EP-OS 17,998, EP-OS 33,581, EP-OS 57,653, EP-OS 89,297, EP-OS 82,987 or EP-OS 100,129).

All of these processes have a substantial disadvantage. In order to obtain low viscosity isocyanato isocyanurates or isocyanurates which are readily soluble in lacquer solvents, it is necessary to interrupt the trimerization reaction at a relatively low degree of trimerization (degree of trimerization = percentage of the isocyanate groups present in the starting isocyanates which have been trimerized) and to carry out thin film distillation, which generally involves complex apparatus, for obtaining a trimerization product which is low in monomers. Otherwise, relatively large quantities of oligoisocyanurates (polyisocyanates with isocyanurate structure containing more than one isocyanurate ring per molecule) would be formed in addition to the low viscosity and readily soluble monomeric isocyanurates which are predominantly desired. This is due to the fact that the isocyanate groups of the starting diisocyanates generally have similar or only slightly different reactivity so the possibility of both isocyanate groups of the starting diisocyanates reacting to form isocyanurates cannot be ruled out.

It was accordingly the underlying aim of the invention to provide new isocyanurate group-containing polyisocyanates which are suitable as lacquer polyisocyanates and which contain substantially no oligomeric trimerization products of the above-mentioned type, i.e., which are composed substantially of tris-isocyanato-monoisocyanurates, and during whose production the trimerization reaction does not have to be interrupted prematurely, i.e., at a degree of trimerization of from about 20 to 40%, in order to achieve this objective.

This aim may be achieved with the isocyanato isocyanurates according to the invention as described in more detail below and by the process for the production thereof in which quite specific starting diisocyanates are used.

SUMMARY OF THE INVENTION

The present invention is directed to isocyanato isocyanurates corresponding to the general formula

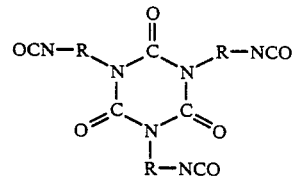

in which R represents radicals which are the same or different, of the type obtained by removing the isocyanate groups from aliphatic-cycloaliphatic diisocyanates with an NCO content of about 20 to 50% by weight, which each contain a sterically unhindered isocyanate group bound to a primary aliphatic carbon atom and a sterically hindered isocyanate group which is bound to a tertiary carbon atom which is part of a cycloaliphatic ring system, the isocyanate groups in said formula being linked with the tertiary carbon atom.

The present invention is also directed to a process for the production of isocyanurate group-containing polyisocyanates by the catalytic trimerization of a portion of the isocyanate groups of organic diisocyanates and optionally terminating the trimerization reaction at the desired degree of trimerization by the addition of a catalytic poison and/or by thermal deactivation of the catalyst used, characterized in that diisocyanates which contain a sterically unhindered isocyanate group bound to a primary aliphatic carbon atom and a sterically hindered isocyanate group which is bound to a tertiary carbon atom which is part of a cycloaliphatic ring system with an NCO content of about 20 to 50% by weight are used as the starting diisocyanates.

Finally, the present invention is directed to the use of the isocyanurate group-containing polyisocyanates according to the invention, optionally blocked with blocking agents for isocyanate groups, as the isocyanate component in polyisocyanate polyaddition products, preferably polyurethane lacquers and most preferably in thermally cross-linkable two-component polyurethane powder lacquers.

DETAILED DESCRIPTION OF THE INVENTION

The use of specific starting diisocyanates in the trimerization reaction is essential to the invention. The starting diisocyanates are aliphatic-cycloaliphatic diisocyanates having an NCO content of about 20 to 50, preferably about 30 to 48% by weight, which contain a sterically hindered cycloaliphatically bound isocyanate group in addition to a sterically unhindered aliphatically bound isocyanate group. Starting isocyanates which are suitable for use in accordance with the invention include those of formula (I) or any mixtures of those of formula (I)

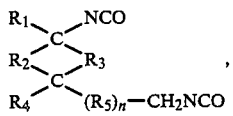
(I)

wherein
$R_1$ represents an alkyl radical containing from 1 to 4 carbon atoms, preferably a methyl radical,
$R_2$ and $R_3$ which may be the same or different each represent a divalent linear or branched saturated hydrocarbon radical containing from 1 to 4, preferably from 1 to 3 carbon atoms, the sum of the carbon atoms in these radicals preferably being from 3 to 6, in particular 4 or 5,
$R_4$ represents hydrogen or an alkyl radical containing from 1 to 4 carbon atoms, preferably hydrogen or a methyl radical,
$R_5$ represents a divalent linear or branched saturated aliphatic hydrocarbon radical containing from 1 to 4, in particular from 1 to 3 carbon atoms
n represents 0 or 1.

Particularly preferred diisocyanates include, for example, 1-isocyanato-1-methyl-4(3)-isocyanatomethylcyclohexane, which is generally present as a mixture of the 4- and 3-isocyanatomethyl-isomers, 1-isocyanato-1-methyl-4-(4-isocyanatobut-2-yl)-cyclohexane or 1-isocyanato-1,2,2-trimethyl-3-(2-isocyanatoethyl)-cyclopentane. However, 1-isocyanato-1-n-butyl-3-(4-isocyanatobut-1-yl)-cyclopentane, 1-isocyanato-1-ethyl-4-n-butyl-4-(4-isocyanatobut-1-yl)-cyclohexane or 1-isocyanato-1,2-dimethyl-3-ethyl-3-isocyanatomethylcyclopentane, for example, are also suitable.

The diisocyanates can be produced, for example, by reacting unsaturated amines corresponding to the general formula (II)

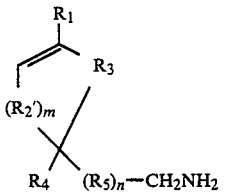
(II)

wherein
$R_2'$ represents a divalent, saturated, linear or branched hydrocarbon radical containing from 1 to 3 carbon atoms
m represents 0 or 1 and
$R_1$, $R_3$, $R_4$, $R_5$ and n have the meaning given above or amino alcohols corresponding to the general formula (III),

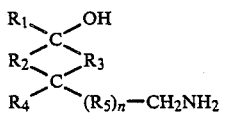
(III)

in which $R_1$, $R_2$, $R_3$, $R_4$, $R_5$ and n have the meaning given above, in a Ritter reaction with hydrocyanic acid to form the diamines corresponding to the general formula (IV),

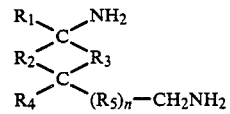
(IV)

The diisocyanates of the general formula (I) are obtained from the diamines of the general formula (IV) by phosgenation.

The unsaturated amines corresponding to the general formula (II) are either known or can be obtained from compounds corresponding to the general formula (V),

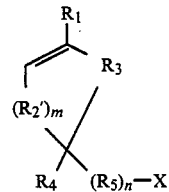
(V)

in which
X represents —CHO or —CN and
$R_1$, $R_2'$, $R_3$, $R_4$, $R_5$ and m and n have the meanings given above, by catalytic hydrogenation.

The basic substances of the general formula (V) can be obtained, for example, by the known Diels-Alder reaction from the corresponding bisolefins containing conjugated double bonds and unsaturated nitriles or aldehydes or by hydroformylation of the corresponding unsaturated hydrocarbons, Thus, for example, the Diels-Alder adduct existing as a position isomer mixture corresponding to formulae (VIa) and (VIb)

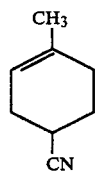
(VIa)

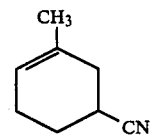
(VIb)

represents the basic substance of 1-isocyanato-1-methyl-4(3)-isocyanatomethylcyclohexane also existing as a position isomer mixture. Also, the compound obtainable by hydroformylation of limonene, corresponding to formula (VII)

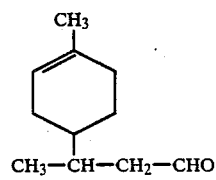
(VII)

the basic substance of 1-isocyanato-1-methyl-4(4-isocyanatobut-2-yl)-cyclohexane. The corresponding basic substance of 1-isocyanato-1,2,2-trimethyl-3-(2-isocyanato-ethyl)-cyclopentane is campholene aldehyde corresponding to formula (VIII)

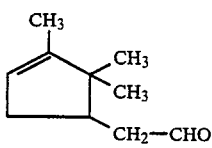
(VIII)

Further basic substances corresponding to the general formula (V) can be obtained analogously to these methods by suitable selection of the starting materials used for the production thereof. Compounds (VI)-(VIII) are also known from the literature ((VI): Chem. Abstr. 71, 112475 F;(VII): EP-A-0008459; (VIII): Berichte der deutschen chemischen Gesellschaft 68B, 1430 (1935)).

The Ritter reaction of the unsaturated amines corresponding to the general formula (II) or of the amino alcohols corresponding to the general formula (III) is carried out in the presence of a strong acid such as sulphuric acid, phosphoric acid, alkyl or aryl sulphonic acids or trifluoroacetic acid. Sulphuric acid is preferably used. The water content of the acid may be between about 5 and 50%, but preferably between about 25 and 35%. About 1 to 3 mol of acid, preferably 2 mol, are used per mol of unsaturated amine. An equimolar quantity or an excess of up to 1 mol of hydrocyanic acid is used with respect to the unsaturated amine corresponding to the general formula (II) or the amino alcohol corresponding to the general formula (III). In a preferred method of operation, the unsaturated amine corresponding to the general formula (II) is added to the acid and the hydrocyanic acid added thereafter. The temperature is maintained between about 0° and 25° C. during addition of the amine and between about 10° and 50° C., preferably between about 30° and 45° C. during addition of the hydrocyanic acid. After a reaction time of about 2 to 10 hours, preferably about 4 to 6 hours, the formamide formed is hydrolyzed by acid and the formed diamine corresponding to the general formula (IV) is liberated by neutralization with a base such as a solution of sodium hydroxide.

The diamine obtained by the Ritter reaction corresponding to the general formula (IV) can be phosgenated in known manner. For this purpose, for example, the diamine is saturated in an inert solvent with carbon dioxide at temperatures of between about 0° and 150° C., preferably between about 80° and 100° C. The resulting addition product is then reacted at about 0° to 200° C., preferably about 120° to 150° C. with phosgene to form the diisocyanate corresponding to the general formula (I). Any inert solvents can be used, of which the boiling temperature is sufficiently high for phosgenation and which have an adequate difference in boiling point from the diisocyanate. Chlorobenzenes, nitrobenzenes, xylenes, tetraline and decaline are preferred.

In a different method of phosgenation, the diamine is added in an inert solvent to a solution of phosgene in the same solvent at temperatures of between about −20° C. and +50° C. The excess phosgene with respect to the diamine should lie between about 2 and 10, preferably between about 4 and 6 mol. A further reaction between the addition product and the diisocyanate takes place at a temperature of about 20° to 200° C., preferably about 120 to 150° C.

The diisocyanates obtained in this way have an NCO content of about 20 to 50, preferably about 30 to 48% by weight and generally represent mixtures of stereo isomers. In addition, the diisocyanates can be mixtures of position isomers, particularly when using unsaturated nitriles corresponding to the general formula (V) (which have been obtained by Diels-Alder reaction) as the basic substance.

Trimerization catalysts which are suitable for the process according to the invention include any compounds used hitherto for this purpose such as phosphines of the type described in DE-OS 1,934,763, alkali phenolates of the type described in GB-PS 1,391,066 or GB-PS 1,386,399, aziridine derivatives combines with tertiary amines of the type described in DE-OS 2,325,826, Mannich bases such as those based on i-nonyl phenol, formaldehyde and dimethyl amine of the type described in U.S. Pat. No. 4,115,373, quaternary ammonium carboxylates of the type described in EP-OS 17,998, quaternary ammonium phenolates of Zwitterionic structure of the type described in U.S. Pat. No. 4,335,219, ammonium phosphonates and phosphates of the type described in DE-OS 3,227,489 or alkali carboxylates of the type described in DE-OS 3,219,608.

Catalysts which are particularly suitable for the process according to the invention include basic alkali metal salts combined with phase transfer catalysts of the type described in more detail by R. Richter, P. Müller and K. Wagner, Die Angewandte Makromolekulare Chemie 113, 1–9 (1983). Potassium acetate complexed with a polyethylene glycol containing on a average from 5 to 8 ethylene oxide units is particularly preferred in this case.

Catalysts which are particularly suitable for the process according to the invention also include quaternary ammonium hydroxides corresponding to the general formula

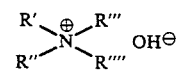

of the type described in DE-OS 2,806,731 and 2,901,479. It is preferable to use quaternary ammonium hydroxides of the specified structure in which the radicals R' to R'''' represent the same or different alkyl groups containing 1 to 20, preferably 1 to 4 carbon atoms which may optionally be substituted with hydroxyl groups and in which two of said radicals R' to R'''' can also form, together with the nitrogen atom and optionally with a further nitrogen or oxygen atom, a heterocyclic ring containing from 3 to 5 carbon atoms, or in which the radicals R' to R''' each represent ethylene radicals which, together with the quaternary nitrogen atom and a further tertiary nitrogen atom, form a bicyclic triethylene diamine framework, provided that the radical R'''' represents a hydroxy alkyl group containing from 2 to 4 carbon atoms in which the hydroxyl group is preferably arranged in the 2-position relative to the quaternary nitrogen atom, wherein in the above-mentioned cases the hydroxyl-substituted radical or the hydroxyl-substituted radicals can also contain other substituents, in particular $C_1$ to $C_4$-alkoxy substituents in addition to the hydroxyl substituent. The last-described catalysts are prepared in a known manner by the reaction of a tertiary amine with an alkylene oxide in an aqueous alcoholic medium (see U.S. Pat. No. 3,995,997, column 2, lines 19 to 44). Trimethylamine, tributylamine, 2-dimethylaminoethanol, triethanolamine, dodecyldimethylamine, N,N-dimethylcyclohexylamine, N-methylpyrrolidine, N-methylmorpholine or 1,4-diazabicyclo-[2,2,2]-octane are mentioned as examples of tertiary amines; ethylene oxide, propylene oxide, 1,2-butylene oxide, styrene oxide or methoxy, ethoxy or phenoxypropylene oxide, for example, may be used as alkylene oxides. N,N,N-trimethyl-N-(2-hydroxyethyl-)ammoniumhydroxide and N,N,N-trimethyle-N-(2-hydroxypropyl)-ammoniumhydroxide are particularly preferred catalysts from this group.

The trimerization reaction can suitably be carried out in the absence, but also easily in the presence of solvents which are inert towards isocyanate groups. Solvents having a low to average boiling point or solvents having a high boiling point can be used depending on the field of application of the products according to the invention. Initially, the products generally remain dissolved when using esters such as ethylacetate or butylacetate, ketones such as acetone or butanone, aromatic substances such as toluene or xylene and halogen hydrocarbons such as methylene chloride and trichloroethylene; whereas, they generally form a second phase or precipitate out in ethers such as diisopropylether or alkanes such as cyclohexane, petroleum ether or ligroin.

The trimerization catalysts are generally used in quantities of about 0.005 to 5% by weight, preferably about 0.01 to 2% by weight, based on the diisocyanate used. If, for example, the preferred catalysts such as complexed potassium acetate or N,N,N-trimethyl-N-(2-hydroxypropyl)-ammonium hydroxide are used, quantities of about 0.05 to 1% by weight, preferably about 0.07 to 0.7% by weight, based on starting diisocyanate, are generally sufficient. The catalysts can be used in a pure form or as a solution. The above-mentioned solvents which are inert towards isocyanate groups as well as dimethyl formamide or dimethylsulphoxide, for example, are suitable as solvents, depending on the type of catalyst. When using carbamic acid derivative-forming hydroxy compounds as co-catalysts, it is advantageous to use them simultaneously as a catalyst solvent. Methanol, ethanol, isopropanol, 2-ethylhexanol or glycols such as 1,2-dihydroxyethane, 1,2-dihydroxypropane, 1,3- and 1,4-dihydroxybutane, 1,6- and 2,5-dihydroxyhexane, 2-ethyl-1,3-dihydroxyhexane or 2,2,4-trimethyl-1,3-dihydroxypentane, for example, are suitable for this purpose.

It is possible, but not necessary to use co-catalysts in the process according to the invention. Suitable co-catalysts in principle are any substances which are known to have a polymerizing effect on isocyanates and are of the type described for example, in DE-OS 2,806,731. The optional co-catalysts are preferably used in a lesser amount relative to the trimerization catalysts used. The hydroxy compounds described, which simultaneously act as carbamic acid derivative-forming co-catalysts and as catalyst solvents represent an exception and can be used in an excess relative to the catalyst.

The reaction temperature required for trimerization is about 20° to 200° C., preferably about 40° to 160° C. and more preferably about 40° to 120° C. in the process according to the invention. The process is most preferably carried out at about 60° to 120° C. in the absence of inert solvents.

The process according to the invention may be carried out in the manner described below:

The starting diisocyanate is placed in a suitable stirrer vessel in the absence of moisture and optionally under inert gas and is mixed with equal parts of a solvent which is inert towards isocyanate groups such as toluene, butyl acetate, diisopropyl ether or cyclohexane. The mixture is then reacted in the presence of the required catalyst or catalyst solution at, for example 60° C. Trimerization begins instantaneously and is demonstrated by an exothermic reaction. The 1-isocyanato-1-methyl-4(3)-isocyanato-methylcyclohexane or the 1-isocyanato-1-methyl-4-(4-isocyanatobut2-yl)-cyclohexane for example are reacted at, for example, 80° C. and the progress of the reaction is followed by titration of the NCO content. The reaction is then interrupted at the desired degree of trimerization. The trimerization reaction is preferably terminated at a degree of trimerization of about 50%, i.e., when the isocyanate group content of the reaction mixture has fallen to about 50% of the starting value.

At that time, the free monomeric diisocyanate content of the reaction mixture is generally below about 2, preferably below about 1% by weight, while the trimerization product is composed predominantly of the desired tris-isocyanato-monoisocyanurates, as demonstrated by gel chromatography.

The trimerization reaction can be terminated, for example, by addition of a catalyst poison of the type mentioned by way of example in the above-mentioned literature references. For example, when using basic catalysts, the reaction is terminated by the addition of a quantity of an acidic chloride such as benzoyl chloride which is at least equivalent to the quantity of catalyst. When using thermally labile catalysts, for example quaternary ammonium hydroxides of the above-mentioned type, deactivation of the catalyst by the addition of a catalyst poison can be omitted because these catalysts undergo thermal decomposition in the course of the reaction. When using such catalysts, the quantity of catalyst and the reaction temperature are preferably selected such that the continuously decomposing catalyst is used up, i.e., decomposed when the said degree of trimerization is reached. The quantity of catalyst required for this purpose and the reaction temperature required for this purpose can be determined by a preliminary test. It is also possible to initially use a smaller quantity of a heat-sensitive catalyst than required for achieving the desired degree of trimerization and subsequently catalyzing the reaction during the course of the trimerization reaction by further incremental additions of catalyst. The subsequently added quantity of catalyst is calculated so that the total quantity of catalyst is used up when the desired degree of trimerization is reached. When using non-polar solvents such as toluene, it is also possible to use suspended catalysts which are removed from the reaction mixture by filtration when the desired degree of trimerization is reached. However, due to the selective reactivity of the isocyanate groups of the starting diisocyanates, the question of destruction or removal of the catalyst at the desired degree of trimerization is far less critical than in the known processes of the prior art. In these processes it is more likely than in the process according to the invention that the second isocyanate group of the starting diisocyanate used will also be trimerized. Thus, the reaction often comes to a stand still itself at a degree of trimerization of 50% without destruction or removal of the catalyst due to the reactivity of the isocyanate group of the starting diisocyanate bound to the tertiary carbon atom.

The reaction mixture can be worked up in various ways, optionally after previous removal of insoluble catalyst constituents, depending on the previous reaction control or on the field of application of the isocyanates used. Thus it is advantageously possible to use an isocyanato isocyanurate produced in solution directly as a lacquer raw material without any cleaning stages, in particular without thin layer distillation, especially at a monomer content of <1% by weight. It is also possible, for example, to further process a trimerized 1-isocyanato-1-methyl-4(3)-isocyanato-methylcyclohexane which is produced without solvent and which forms a rigid resin after cooling, directly as a lacquer isocyanate component whith a low monomer content. It may also be advantageous to use a solvent mixture such as diisopropylether/pretoleum ether in which the trimerization product precipitates as a crystalline white powder during the cooling process and can then be filtered. However, the solvent used during trimerization can be removed by distillation after complete reaction of the primarily bound NCO groups of a starting diisocyanate such as 1-isocyanato-1-methyl-4-(4-isocyanatobut-2-yl)-cyclohexane.

The products according to the invention represent valuable starting materials for the production of polyisocyanate polyaddition products, preferably polyurethane plastics by reaction with compounds containing isocyanate-reactive hydrogens according to the isocyanate polyaddition process, in particular for the production of single component or two-component polyurethane lacquers by reaction with polyols.

Preferred reactants for the products of the process according to the invention (which may be present in blocked form) during the production of polyurethane lacquers including the polyhydroxy polyesters and polyethers, polyhydroxy polyacrylates and optionally lower molecular polyvalent alcohols known per se in polyurethane lacquer technology. Polyamines, in particular in blocked form as polyketimines or oxazolidines, are also possible reactants for the products of the process according to the invention. The proportions in which the polyisocyanates according to the invention and the above-mentioned reactants are reacted during the production of polyurethane lacquers are generally selected in such a way that about 0.8 to 3, preferably about 0.9 to 1.1 hydroxy, amino and/or carboxyl groups are allotted to one (optionally blocked) isocyanate group.

To accelerate curing, the catalysts which are conventional in isocyanate chemistry can be used in a known manner. Examples include tertiary amines such as triethylamine, pyridine, methylpyridine, benzyldimethylamine, N,N-dimethylamino-cyclohexane, N-methylpiperidine, pentamethyldiethylene triamine, 1,4-diazabicyclo[2,2,2]-octane or N,N'-dimethylpiperazine and metal salts such as iron (III)-chloride, zinc-chloride, zinc2-ethylcaproate, tin (II)-2-ethylcaproate, dibutyl tin(IV)-dilaurate or molybdenum glycolate.

The isocyanato isocyanurates according to the invention can also be used as valuable starting materials for two-component polyurethane stoving lacquers. For this purpose, they can be used in blocked form by reaction with the known blocking agents. However, due to the inactivity of the tertiary bound isocyanate groups of the polyisocyanates according to the invention, it is particularly advantageous that they can be used in two-component stoving lacquers without previous masking of the isocyanate groups with blocking agents.

The blocking stage of the process may therefore be omitted in these systems which is particularly desirable since no blocking agent is released during the stoving process. Thus, for example, it is preferable to use the isocyanato isocyanurate of 1-isocyanato-1-methyl-4(3)-isocyanatomethylcyclohexane having a melting range above about 100° C. in unblocked form as the isocyanate component for powder lacquers. However, if blocking of the NCO groups is desired, known methods can be used. The polyisocyanate is completely or partially blocked with suitable blocking agents, preferably at elevated temperatures (for example about 40° to 160° C.), optionally in the presence of a suitable catalyst such as tertiary amines or metal salts of the type already mentioned by way of example.

Suitable blocking agents include monophenols such as phenol; the cresols; the trimethylphenols; the tertiary butyl phenols; tertiary alcohols such as tertiary butanol, tertiary amyl alcohol and dimethylphenylcarbinol; compounds which easily form enols such as acetoacetic ester, acetyl acetone and malonic acid derivatives, particularly malonic acid diethyl ester; secondary aromatic amines such as N-methylaniline, the N-methyltoluidines, N-phenyltoluidine and N-phenylxylidine; imides such as succinimide; lactams such as ε-caprolactam and δ-valerolactam; oximes such as butanone oxime and cyclohexanone oxime; mercaptanes such as methylmercaptane, ethylmercaptane, butylmercaptane, 2-mercaptobenzthiazole, α-naphthylmercaptan and dodecylmercaptane, or triazoles such as 1H-1,2,4--triazole.

To produce the lacquer binders, optionally blocked polyisocyanates, polyfunctional reactants, catalyst and optionally conventional additives such as pigments, dyes, fillers and flow agents are thoroughly mixed and homogenized on a conventional mixer unit, such as a sand mill either with or without solvents and diluents.

The paints and coating agents can be applied to the article to be coated in solution or from the melt or in solid form by conventional methods such as brushing, rolling, casting, spraying, by the whirl sinter method or the electrostatic powder spraying method.

The lacquers containing the polyisocyanates according to the invention produce films which adhere surprisingly well to metallic substrates and are particularly fast to light, thermally color stable and very wear-resistant. Furthermore, they are distinguished by high rigidity, elasticity, very good stability to chemicals, high luster, excellent resistance to weathering good pigmentability.

The following examples illustrate the invention. All percentages are percentages by weight.

EXAMPLES

The following starting materials were used in the examples below:

Diisocyanate I
(1-isocyanato-1-methyl-4-(4-isocyanatobut-2-yl)cyclohexane):

(a) Production of 1-amino-1-methyl-4-(4-aminobut-2-yl)cyclohexane:

830 g of 3-[1-methylcyclohexen-4-yl]-butyraldehyde were dissolved in 800 ml of liquid ammonia in a stirrer autoclave and hydrogenated over 50 g of Raney nickel iron at 90° C. and a hydrogen pressure of 100 bar. After evaporation of the solvent, the mixture was filtered from the catalyst and distilled under vacuum. 720 g (86%) of 3-(1-methylcyclohexen-4-yl)-butylamine, b.p.$_{10}$ 120° C. were obtained.

660 g of this amine were added dropwise to 1200 g of 70% sulphuric acid at 5 to 10° C. 170 ml of hydrocyanic acid were then added dropwise at 30 to 35° C., the mixture was stirred for a further 4 hours at 45° C. and the excess hydrocyanic acid was distilled off under vacuum. 300 ml of water were then added and the mixture was heated for 3 hours to reflux, rendered alkaline with 1400 ml of 45% sodium hydroxide solution and decanted from the precipitated salt. The phases were separated, the salts and the aqueous phase were extracted twice with toluene and the mixture was distilled under vacuum. 656 g (90%) of 1-amino-1-methyl-4-(4-aminobut-2-yl)cyclohexane, b.p.$_{10}$ 135 to 137° C. were obtained.

(b) Production of
1-isocyanato-1-methyl-4-(4-isocyanatobut-2-yl)-cyclohexane:

A solution of 46 g of 1-amino-1-methyl-[4-aminobut-2-yl]cyclohexane in 80 ml of dichlorobenzene was added dropwise to a solution of 125 g of phosgene in 200 ml of dichlorobenzene at 0° C. The mixture was heated to 150° C. in 2 hours while introducing phosgene and phosgene was then introduced for an additional 3 hours at 150° C. The remaining phosgene was blown out with nitrogen. The solvent was distilled off under vacuum and the residue was fractionated under vacuum. 50 g (85%) of 1-isocyanato-1-methyl-4-(4-isocyanatobut-2-yl)cyclohexane, b.p.$_{0.1}$ 130° C. were obtained.

Diisocyanate II (1-isocyanato-1-methyl-4 (3)-isocyanatomethylcyclohexane):

(a) Production of
1-amini-1-methyl-4(3)-aminomethylcyclohexane:

605 g of 4(5)-cyano-1-methylcyclohexene were dissolved in 500 ml of liquid ammonia in a stirrer autoclave and hydrogenated at 90° C. and at a hydrogen pressure of 100 bar over 40 g of Raney nickel iron. After evaporating the ammonia, the mixture was filtered from the catalyst and distilled under vacuum. 550 g (88%) of 4(5)-aminomethyl-1-methylcyclohexene, b.p.$_{10}$ 78° to 80° C. were obtained. The ratio by weight of the 4- and 5-isomers was about 80:20.

1125 g of this unsaturated amine were added dropwise to 2650 g of 70% sulphuric acid at between 10° and 25° C., and 360 ml of hydrocyanic acid were added dropwise at 40° to 45° C. The mixture was stirred for a further 4 hours at 45° C., the unreacted hydrocyanic acid was distilled off under vacuum and 2 l of water were added. The mixture was then heated for 3 hours to reflux, rendered alkaline with 2.7 l of 45% sodium hydroxide solution and decanted from the precipitated salt. The organic phase was separated, the salt and the aqueous phase were washed twice with toluene and the mixture was distilled over an 80 cm column under vacuum. 907 g (71%) of 1-amino-1-methyl-4(3)-aminomethylcyclohexane, b.p.$_{10}$ 95° to 105° C. and 172 g (13%) of 4(3)-aminomethyl-1-methyl-cyclohexanol, b.p.$_{10}$ 115° to 120° C. were obtained.

(b) Production of
1-isocyanato-1-methyl-4(3)-isocyanatomethylcyclohexane:

A solution of 71 g of 1-amino-1-methyl-4(3)-aminomethylcyclohexane in 150 ml of dichlorobenzene was added dropwise to a solution of 250 g of phosgene in 350 ml of dichlorobenzene at 0° C. The mixture was heated to 150° C. in 2 hours while introducing phosgene and phosgene was then introduced for an additional 7 hours at 150° C. The phosgene was blown out with nitrogen, the solvent was distilled off under vacuum and the residue was fractionated under vacuum.

73 g (75%) of 1-isocyanato-1-methyl-4 (3)-isocyanato-methylcyclohexane, b.p.$_{0.1}$ 95° to 103° C. were obtained. The ratio by weight of the 4- and 3-isomers was about 80:20.

Catalyst I 2.7 g of 1,4,7,10,13,16-hexaoxacyclooctadecane and 1.0 g of potassium acetate were dissolved in methanol. After concentration under vacuum, the catalyst was obtained as a crystalline complex.

Catalyst II 0.5 molar solution of potassium acetate in polyethylene glycol having an average molecular weight of 370.

Catalyst III

10% solution of 2-hydroxypropyl-trimethylammoniumhydroxide in 2-ethyl-1,3-dihydroxyhexane/1,3-dihydroxybutane (ratio by weight of the solvents: 4:1).

Example 1

1.0 g of catalyst I was stirred into a solution of 250 g of diisocyanate I in 250 g of anhydrous toluene in the absence of moisture. The reaction mixture was then heated to 80° C. After stirring for 4 hours at this temperature, the NCO content of the solution had dropped from 17.8% to 8.8%. The mixture was heated briefly (15 minutes) to boiling temperature and the crystalline complex was then filtered off. The clear yellowish solution only contained one main component possessing the molecular ion $M^+ = 708$ (corresponding to trisisocyanato-monoisocyanurate) in the mass spectrum in addition to toluene in the gel chromatogram. The content of free diisocyanate I was less than 0.3%. After removing the solvent, a tough viscous resin having an NCO content of 17.6% was obtained.

Example 2

1.0 g of catalyst I was stirred into a solution of 250 g of diisocyanate II in 250 g of anhydrous toluene in the absence of moisture. The reaction mixture was then heated to 80° C. with stirring. After stirring for 8 hours at this reaction temperature, the NCO content of the solution had fallen from 21.6% to 11.0%. 0.39 g of benzoyl chloride were added, the mixture was stirred for 30 minutes and the crystalline complex was filtered off. The yellowish solution was then freed from a solvent by distillation. A slightly yellowish, solid residue was obtained which was digested with 100 ml of n-hexane and then filtered and washed with 50 ml of n-hexane.

After drying, 224 g of a white solid product having an NCO content of 21.2% and a melting point of 128° to 130° C. remained. One main component showing the molecular ion $M^+ = 582$ (corresponding to the trisisocyanato-monoisocyanurate) in the mass spectrum was found in the gel chromatogram.

Example 3

In accordance with Example 2, 250 g of diisocyanate II were reacted in 250 g of anhydrous diisopropylether at 68° C. using 0.5 ml of catalyst II. After attaining an NCO content in the reaction mixture of 10.4% (degree of trimerization: 52%), the mixture was allowed to cool and a finely crystalline white solid product was precipitated. The suspension was stirred with 500 ml of petroleum ether, filtered and dried under vacuum. 229 g of a white crystalline solid product having an NCO content of 20.6% and a melting point of 125° to 127° C. were obtained. The gel chromatogram showed that this was almost exclusively the corresponding trisisocyanato-monoisocyanurate.

Example 4

582 g of diisocyanate II were reacted at 65° C. with 13 ml of catalyst III. The exothermic reaction mixture was kept at 80° C. by cooling and later was heated to this temperature. The mixture was subsequently catalyzed with 5 ml of catalyst solution after 3 hours at an NCO content of 24.7%. After 6 hours, when the reduction of the NCO content had come to a virtual standstill at a value of 22.1% (degree of trimerization: 49%), the viscous mass was poured onto a metal sheet. A glass-like rigid resin with an NCO content of 20.3% and a melting range of 90° to 110° C. was obtained. The content of monomeric diisocyanate was less than 2%.

Example 5

194 g of diisocyanate II were dissolved in 48.5 g of toluene and then reacted at 70° C. with 6 ml of catalyst solution III. The reduction of the NCO content came to a standstill after about 5 hours at a reaction temperature of 80° C. (degree of trimerization: 56%). An 80% polyisocyanate solution having an NCO content of 14.7%, a viscosity $\eta(23° C.)$ of 1700 mPas and a monomeric diisocyanate content of less than 1% was obtained.

Examples of Use

Example 6

51 parts by weight of a hydroxyl group-containing polyester based on 58.2 parts by weight of teraphthalic acid, 33.3 parts by weight of neopentylglycol, 4.6 parts by weight of 1,6-dihydroxyhexane and 3.4 parts by weight of trimethylol propane having an OH number of 50 and a hydroxyl equivalent weight of 1120, 9 parts by weight of the polyisocyanate produced according to Example 4 as hardener and 40 parts by weight of a conventional commercial titanium dioxide pigment (rutile) were melted and homogenized in an extruder at about 120° C. The polyhydroxy polyester and the polyisocyanate were metered in equivalent proportions by weight. Once the melt had set, the product was ground, applied to test metal sheets by means of an electrostatic sprayer and cured within 15 minutes at 200° C.

The following lacquer properties were found at a layer thickness of 54 to 56 $\mu$m:
Luster: 91%
(Gardner, 60° Angle of Reflection)
Acetone Solubility: 2
(50 double strokes with acetone-impregnated cotton pad, 0=no change, 2=swollen)
Bending Test: 0
(0=no change, 2=torn)
Grid Test or "square cut adhesion test": GT 0/0 (DIN 53 151, 0=no loss of adhesion, 4=total loss of adhesion, first value before tearing off Sellotape, second value after tearing off Sellotape.
Erichsen "cupping" test: >10 mm
(DIN 53 156)
Whiteness: 74.9; after 15 minutes at 200° C. - 71.4
(according to Berger/Elrephomat)
Gel Time: 271 sec at 180° C.
(DIN 55 990 part 8, item 5.1)
Pourability: O.K.
(DIN 55 990 part 7, 2 weeks at 45° and 50° C.)

Example 7

A powder lacquer was produced from 51 parts by weight of the hydroxyl group-containing polyester described in Example 6, 9 parts by weight of a polyisocyanate produced according to Example 2 and 40 parts by weight of a conventional commercial titanium dioxide pigment in the manner described in Example 6. The coated test metal sheets after stoving for 15 minutes at 200° C. in a layer thickness of 56 to 60 $\mu$m had the following test values:
Luster: 92%
Acetone Solubility: 2
Bending Test: 0
Grid Test: GT 0/0
Erichsen "cupping" test: >10 mm
Whiteness: 77.2; after 15 minutes at 200° C. - 75.4
Gel Time: 252 seconds at 180° C.
Pourability: O.K.

Example 8

A powder lacquer was prepared in the manner described in Example 6 from 47 parts by weight of the hydroxyl group-containing polyester used in Example 6, 12 parts by weight of the polyisocyanate produced according to Example 4 as hardener, 39 parts by weight of the titanium dioxide pigment used in Example 6 and 2 parts by weight of tin(II)-2-ethyl-caproate as catalyst. The following properties were found after stoving the lacquer on test metal sheets for 15 minutes at 200° C. in a layer thickness of 50 to 52 $\mu$m:
Luster: 92%
Acetone Solubility: 2
Bending Test: 0
Grid Test: GT 0/0
Erichsen "cupping" test: 10 mm
Whiteness: 77.2; after 15 minutes at 200° C. - 75.2
Gel Time: 222 seconds at 180° C.
Pourability: O.K.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An isocyanurate group-containing polyisocyanate corresponding to the formula wherein
R represents a radical corresponding to the formula

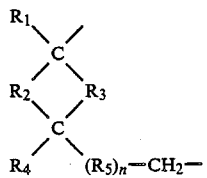

wherein
- $R_1$ represents an alkyl radical containing 1 to 4 carbon atoms,
- $R_2$ and $R_3$ which may be the same or different represent a linear or branched divalent saturated hydrocarbon radical containing 1 to 4 carbon atoms,
- $R_4$ represents hydrogen or an alkyl radical containing 1 to 4 carbon atoms,
- $R_5$ represents a linear or branched, saturated divalent hydrocarbon radical containing 1 to 4 carbon atoms, and
- n represents 0 or 1.

2. The isocyanurate group-containing polyisocyanate of claim 1 wherein
- $R_1$ represents a methyl radical,
- $R_2$ and $R_3$ which may be the same or different represent linear divalent saturated hydrocarbon radicals containing from 1 to 3 hydrocarbon atoms, provided that the sum of the number of carbon atoms in the radicals $R_2$ and $R_3$ is 4 or 5,
- $R_4$ represents a hydrogen atom,
- $R_5$ represents a linear or branched, saturated divalent hydrocarbon radical containing from 1 to 3 carbon atoms, and
- n represents 0 or 1.

3. The isocyanurate group-containing polyisocyanate of claim 2 wherein
- $R_2$ represents ethylene or trimethylene and the sum of the number of carbon atoms in the radicals $R_2$ and $R_3$ is 4, and
- n represents 0.

4. The isocyanurate group-containing polyisocyanate of claim 2 wherein
- $R_2$ and $R_3$ both represent ethylene,
- $R_5$ represents isoproylene with the branched carbon atom vicinal to the cyclohexane ring, and
- n represents 1.

* * * * *